US012649924B2

(12) United States Patent (10) Patent No.: US 12,649,924 B2
Kim et al. (45) Date of Patent: Jun. 9, 2026

(54) COMPOSITION FOR INHIBITING GROWTH OF CANCER STEM CELLS, CONTAINING WDR34 INHIBITOR, AND USE THEREOF

(71) Applicant: KOREA ATOMIC ENERGY RESEARCH INSTITUTE, Daejeon (KR)

(72) Inventors: Rae Kwon Kim, Sejong (KR); In Gyu Kim, Daejeon (KR); Yeon Jee Kahm, Hwaseong-si (KR)

(73) Assignee: KOREA ATOMIC ENERGY RESEARCH INSTITUTE, Daejeon (KR)

( * ) Notice: Subject to any disclaimer, the term of this patent is extended or adjusted under 35 U.S.C. 154(b) by 949 days.

(21) Appl. No.: 17/851,500

(22) Filed: Jun. 28, 2022

(65) Prior Publication Data

US 2022/0403395 A1 Dec. 22, 2022

Related U.S. Application Data

(63) Continuation-in-part of application No. PCT/KR2020/018890, filed on Dec. 22, 2020.

(30) Foreign Application Priority Data

Dec. 31, 2019 (KR) ........................ 10-2019-0179659

(51) Int. Cl.
| | |
|---|---|
| *C12N 15/113* | (2010.01) |
| *A61P 11/00* | (2006.01) |
| *A61P 25/00* | (2006.01) |
| *A61P 35/00* | (2006.01) |
| *A61P 35/04* | (2006.01) |
| *G01N 33/50* | (2006.01) |

(52) U.S. Cl.
CPC .......... *C12N 15/1138* (2013.01); *A61P 11/00* (2018.01); *A61P 25/00* (2018.01); *A61P 35/00* (2018.01); *A61P 35/04* (2018.01); *G01N 33/5011* (2013.01); *G01N 33/5029* (2013.01); *C12N 2310/14* (2013.01); *C12N 2320/31* (2013.01)

(58) Field of Classification Search
None
See application file for complete search history.

(56) References Cited

U.S. PATENT DOCUMENTS

| | | |
|---|---|---|
| 8,637,240 B2 | 1/2014 | Tian et al. |
| 2010/0113297 A1 | 5/2010 | Lidereau et al. |
| 2010/0273660 A1* | 10/2010 | Zender ................. C12Q 1/6886 |
| | | 506/25 |
| 2011/0105340 A1 | 5/2011 | Tian et al. |
| 2012/0052487 A9* | 3/2012 | Khvorova .............. A61P 37/02 |
| | | 536/23.1 |

FOREIGN PATENT DOCUMENTS

| | | |
|---|---|---|
| JP | 2010-518878 | 6/2010 |
| KR | 10-2016-0047735 | 5/2016 |
| WO | 2011/038400 | 3/2011 |

OTHER PUBLICATIONS

Lee et al. Biomedicines 11, 356, pp. 1-22 (Year: 2023).*
Fakhr Cancer Gene Therapy 23. 73-82 (Year: 2016).*
Cakan et al. Therapeutic Antisense Oligonucleotides in Oncology 16, pp. 1-35 (Year: 2024).*
Yamamoto et al., "Evaluation of tryptophan-aspartic acid repeat-containing protein 34 as a novel tumor-suppressor molecule in human oral cancer", Biochemical and Biophysical Research Communications 495: 2469-2574 (Dec. 24, 2017).
Sun, Jing-Hui et al.,"Liver cancer stem cell markers: progression and therapeutic implications", World Journal of Gastroenterology,Apr. 7, 2016, vol. 22, No. 13, pp. 3547-3557.
Luo, Xiaoling et al., "WDR34 activates Wnt/Beta-catenin signaling in hepatocellular carcinoma", Digestive Diseases and Sciences, Mar. 15, 2019(online publication date),vol. 64 No.9,pp. 2591-2599.
Dao-Jun Hu et al., "High WDR34 mRNA expression as a potential prognostic biomarker in patients with breast cancer as determined by integrated bioinformatics analysis", Oncology Letters 18: 3177-3187(Jul. 18, 2019).
Anne T. Collins et al., "Prospective Identification of Tumorigenic Prostate Cancer Stem Cells", Cancer Research • Jan. 2006.
Dominique Bonnet et al., "Human acute myeloid leukemia is organized as a hierarchy that originates from a primitive hematopietic cell", Nature Medicine vol. 3, No. 7, Jul. 1997.
Lucia Ricci-Vitiani et al., "Identification and expansion of human colon-cancer-initiating cells", Nature vol. 445, Jan. 4, 2007.
Monya Baker, "Melanoma in mice casts doubt on scarcity of cancer stem cells", Nature vol. 456, Dec. 4, 2008.
Adam Nagy et al., "Validation of miRNA prognostic power in hepatocellular carcinoma using expression data of independent datasets", SCientifiC RepoRts, (2018) 8:9227.
Roxanne Khamsi, "Cancer stem cells produce brain tumours", Nature, Nov. 17, 2004.
John E. Dick, "Breast cancer stem cells revealed", PNAS vol. 100, Apr. 1, 2003.

* cited by examiner

*Primary Examiner* — Brian Whiteman
(74) *Attorney, Agent, or Firm* — LEX IP MEISTER, PLLC

(57) ABSTRACT

The present invention relates to a composition for inhibiting the growth of cancer stem cells, and a use thereof. A WDR34 inhibitor of the present invention inhibits the conversion of cancer cells into cancer stem cells and exhibits activity of inhibiting self-renewal, invasion, and migration of cancer stem cells, and thus can be effectively used as a cancer cell growth or metastasis inhibitor or a cancer stem cell growth inhibitor.

9 Claims, 10 Drawing Sheets

Specification includes a Sequence Listing.

SEQUENCE LISTING

<160> NUMBER OF SEQ ID NOS: 3

<210> SEQ ID NO 1

<211> LENGTH: 1611
<212> TYPE: DNA
<213> ORGANISM: Artificial Sequence
<220> FEATURE:
<223> OTHER INFORMATION: Synthesized

<400> SEQUENCE: 1
atggcaaccc gcgcgcagcc ggggccactc agccaggcgg gaagcgctgg tgttgcggcg        60
ctggcgacag tcggggttgc gagcggcccg gggccggggc ggccaggcc gctgcaggac        120 gagaccctgg gtgtggcgtc cgtgccctcg cagtggaggg ccgtccaggg catccgcggg        180
gagacgaaaa gttgccagac ggccagcatt gccactgcca gtgcatccgc ccaggccagg        240
aatcatgtgg acgcccaggt gcagacggag gcccccgtgc ctgtcagcgt gcagcccccg        300
tcccagtacg acatacccag gcttgcagcc tttcttcgga gagtggaggc catggtcatc        360
cgagagctga acaagaattg gcagagccac gcgtttgatg gcttcgaggt gaactggacc        420
gagcagcagc agatggtgtc ttgtctgtat accctgggct accgccagc ccaagcgcag         480 ggtctgcatg tgaccagcat ctcctggaac tccactggct ctgtggtggc ctgtgcctac        540
ggccggctgg accatgggga ctggagcacg cttaagtcct tcgtgtgtgc ctggaacctg        600
gaccggcgag acctgcgtcc ccagcaaccg tcggccgtgg tggaggtccc cagcgctgtc        660
ctgtgtctgg ccttccaccc cacgcagccc tcccacgtcg caggagggct gtacagtggt        720
gaggtgttgg tgtgggacct gagccgtctt gaggacccgc tgctgtggcg cacaggcctg        780
acggatgaca cccacacaga ccctgtgtcc caggtggtgt ggctgcccga gcctgggcac        840
agccaccgct tccaggtgct gagtgtggcc actgacggga aggtgctact ctggcagggc        900
atcggggtag gccagctgca gctcacagag ggcttcgccc tggtcatgca gcagctgcca        960
cggagcacca agctcaagaa gcatccccgc ggggagaccg aggtgggcgc cacggcagtg        1020
gccttctcca gctttgaccc taggctgttc attctgggca cggaaggcgg cttcccgctc        1080
aagtgttccc tggcagctgg agaggcagcc ctcacgcgga tgcccagctc cgtgcccctg        1140
cgggccccag cacagtttac cttctccccc cacggcggtc ccatctactc tgtgagctgt        1200
tcccccttcc acaggaatct cttcctgagc gctgggactg acgggcatgt ccacctgtac        1260
tccatgctgc aggcccctcc cttgacttcg ctgcagctct ccctcaagta tctgtttgct        1320
gtgcgctggt ccccagtgcg gcccttggtt tttgcagctg cctctgggaa aggtgacgtg        1380
cagctgtttg atctccagaa aagctcccag aaacccacag ttttgatcaa gcaaacccag        1440
gatgaaagcc ctgtctactg tctggagttc aacagccagc agactcagct cttggctgcg        1500
ggcgatgccc agggcacagt gaaggtgtgg cagctgagca cagagttcac ggaacaaggg        1560
ccccgggaag ctgaggacct ggactgcctg gcagcagagg tggcggcctg a               1611

<210> SEQ ID NO 2
<211> LENGTH: 19
<212> TYPE: RNA
<213> ORGANISM: Artificial Sequence
<220> FEATURE:
<223> OTHER INFORMATION: Synthesized

<400> SEQUENCE: 2
ggagcacgcu uaaguccuu                                                     19

<210> SEQ ID NO 3
<211> LENGTH: 19
<212> TYPE: RNA
<213> ORGANISM: Artificial Sequence -continued

```
<220> FEATURE:
<223> OTHER INFORMATION: Synthesized

<400> SEQUENCE: 3
aaggacuuaa gccuccucc                                                              19
```

COMPOSITION FOR INHIBITING GROWTH OF CANCER STEM CELLS, CONTAINING WDR34 INHIBITOR, AND USE THEREOF

CROSS-REFERENCES TO RELATED APPLICATION

This application is a Bypass Continuation-In-Part Application of a National Stage application of PCT/KR2020/018890 filed on Dec. 22, 2020, which claims priority to Korean Patent Application No. 10-2019-0179659 filed on Dec. 31, 2019, the contents of which are incorporated herein by reference.

TECHNICAL FIELD

The present invention relates to a composition for inhibiting the growth of cancer stem cells, and uses thereof.

BACKGROUND ART

Similar to normal stem cells present in normal cells, about 1% to 2% of cancer stem cells are present in cancer tissue. The cancer stem cells were revealed to be present in leukemia by Dr. John E. Dick in 1997 (Nat Med, 1997), and subsequently, the presence of cancer stem cells was also reported in breast cancer (PNAS, 2003), brain tumor (Nature, 2004), prostate cancer (Cancer Res, 2005), colorectal cancer (Nature, 2007), and melanoma (Nature, 2008). Such cancer stem cells have self-renewal ability, which is a property of normal stem cells, and thus can cause cancer-related cells, which have been reduced or disappeared by an anticancer treatment, to self-renew, thereby causing cancer to recur. Moreover, such cancer stem cells have migration and invasion ability and thus can cause cancer metastasis. Due to the aforementioned properties of the cancer stem cells, the cancer stem cells have significantly emerged as a major cause of malignant transformation of cancer, resistance to an anticancer treatment, and cancer metastasis.

In the case of normal stem cells, the growth and differentiation of cells are regulated by a tightly regulated self-renewal mechanism, whereas cancer stem cells are affected by tumor microenvironmental factors around cancer cells to cause abnormal self-renewal and differentiation, and, due to such a phenomenon, can acquire resistance to anticancer treatments such as a radiation treatment and chemotherapy with anticancer drugs, and can cause cancer metastasis and recurrence.

Despite the high need to target and treat cancer stem cells for an anticancer treatment, since most of the anticancer drugs currently on the market act with a mechanism to inhibit known target genes in cancer cells or to inhibit cancer-related cell signaling in cancer cells, anticancer drugs that act with such a mechanism have difficulties in being applied to anticancer treatments due to mutations in cancer-related genes or proteins and complex cell signaling. Therefore, in order to increase the therapeutic effect and survival rate of cancer patients, a therapeutic method targeting cancer stem cells is required.

WDR34 genes belong to the WD repeat domain (WDR) family, are down-regulated in oral squamous cell carcinoma (OSCC) compared to normal tissues, and have been reported as a tumor suppressor which is expected to play an important role in controlling tumor progression in OSCC (Yamamoto et al., Evaluation of tryptophan-aspartic acid repeat-containing protein 34 as a novel tumor-suppressor molecule in human oral cancer. Biochemical and Biophysical Research Communications (2018) 495(4): 2469-2574). Moreover, it is known that WDR34 is located in cells and plays a role in a cell cycle, apoptosis, gene regulation, and the like.

Under such a technical background, the present inventors have made an effort to develop anticancer drugs targeting cancer stem cells, and, as a result, have confirmed that the expression level of WD repeat domain 34 (WDR34) is related to the properties of cancer stem cells, thereby completing the present invention.

DISCLOSURE OF THE INVENTION

Technical Problem

Accordingly, an object of the present invention is to provide a composition for inhibiting the growth of cancer stem cells, the composition containing a WDR34 inhibitor, that can be used to significantly improve the therapeutic effect on cancer through inhibition of the growth, renewal, invasion, and migration of cancer-related cells.

Another object of the present invention is to provide a pharmaceutical composition for preventing or treating cancer, the pharmaceutical composition containing the aforementioned WDR34 inhibitor.

Still another object of the present invention is to provide a method for screening a substance for inhibiting cancer recurrence or cancer metastasis by using a cell line expressing the aforementioned WDR34.

Still another object of the present invention is to provide a composition for assisting a radiation anticancer treatment, the composition comprising the aforementioned WDR34 inhibitor.

Technical Solution

In order to achieve the objects, an aspect of the present invention provides a composition for inhibiting the growth of cancer stem cells, the composition comprising a WD repeat domain 34 (WDR34) inhibitor as an active ingredient.

Another aspect of the present invention provides a pharmaceutical composition for preventing or treating cancer, the pharmaceutical composition comprising a WDR34 inhibitor as an active ingredient.

Still another aspect of the present invention provides a method for screening a substance for inhibiting cancer recurrence or cancer metastasis by using a cell line overexpressing WDR34.

Still another aspect of the present invention provides a composition for assisting a radiation anticancer treatment, the composition comprising a WDR34 inhibitor as an active ingredient.

Advantageous Effects

The WDR34 inhibitor according to the present invention inhibits the transformation of cancer cells into cancer stem cells, and exhibits the activity to inhibit the self-renewal, invasion, and migration of cancer stem cells, and thus can be usefully used as a cancer cell growth or metastasis inhibitor or a cancer stem cell growth inhibitor.

Moreover, the present invention is a technique in which by the concurrent treatment with conventional anticancer drugs or radiation treatments, anticancer activity can be further increased and the used amount of anticancer drugs can be drastically reduced, and thus the side effects caused by the use of anticancer drugs can be reduced and the effect of a radiation anticancer treatment on subjects who are difficult to treat due to resistance to conventional radiation treatments can be significantly improved, and the technique is useful for a treatment of cancer, which has poor prognoses for conventional anticancer treatments.

Figure 7:
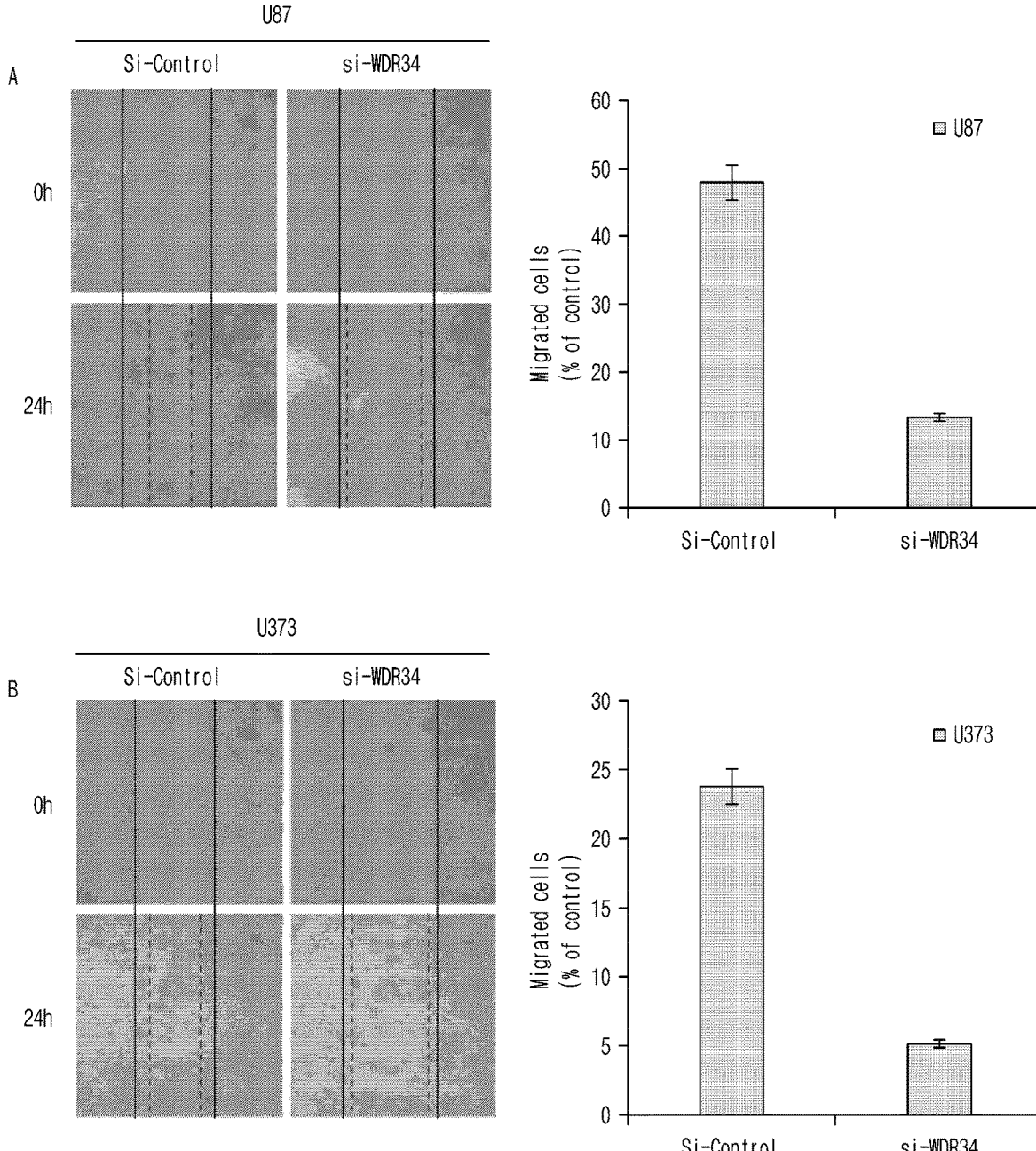

A and B of FIG. 7 show the results of treating brain cancer stem cells (U87-CD133+, U373-CD133+) with WDR34 siRNA and then checking the migration ability of the cancer stem cells through scratch analysis.

Figure 8:
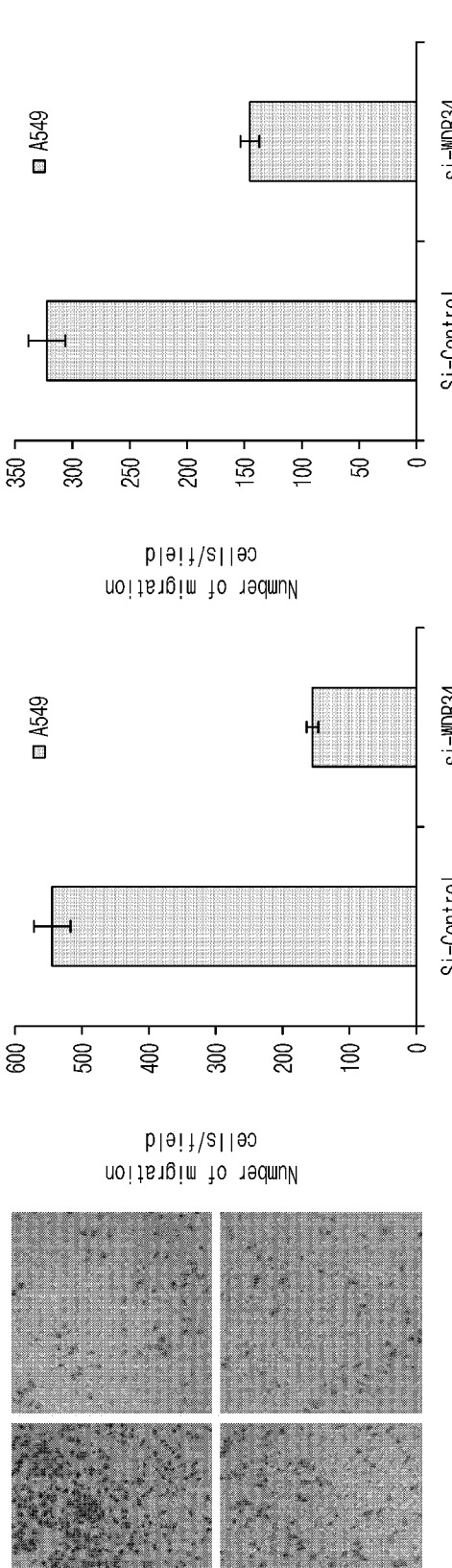

FIG. 8 shows the migration and invasion ability of cancer stem cells after treating lung cancer stem cells (A549-ALDH1+) with WDR34 siRNA, as a result of microscopic observation and the number of migrated cells.

Figure 9:
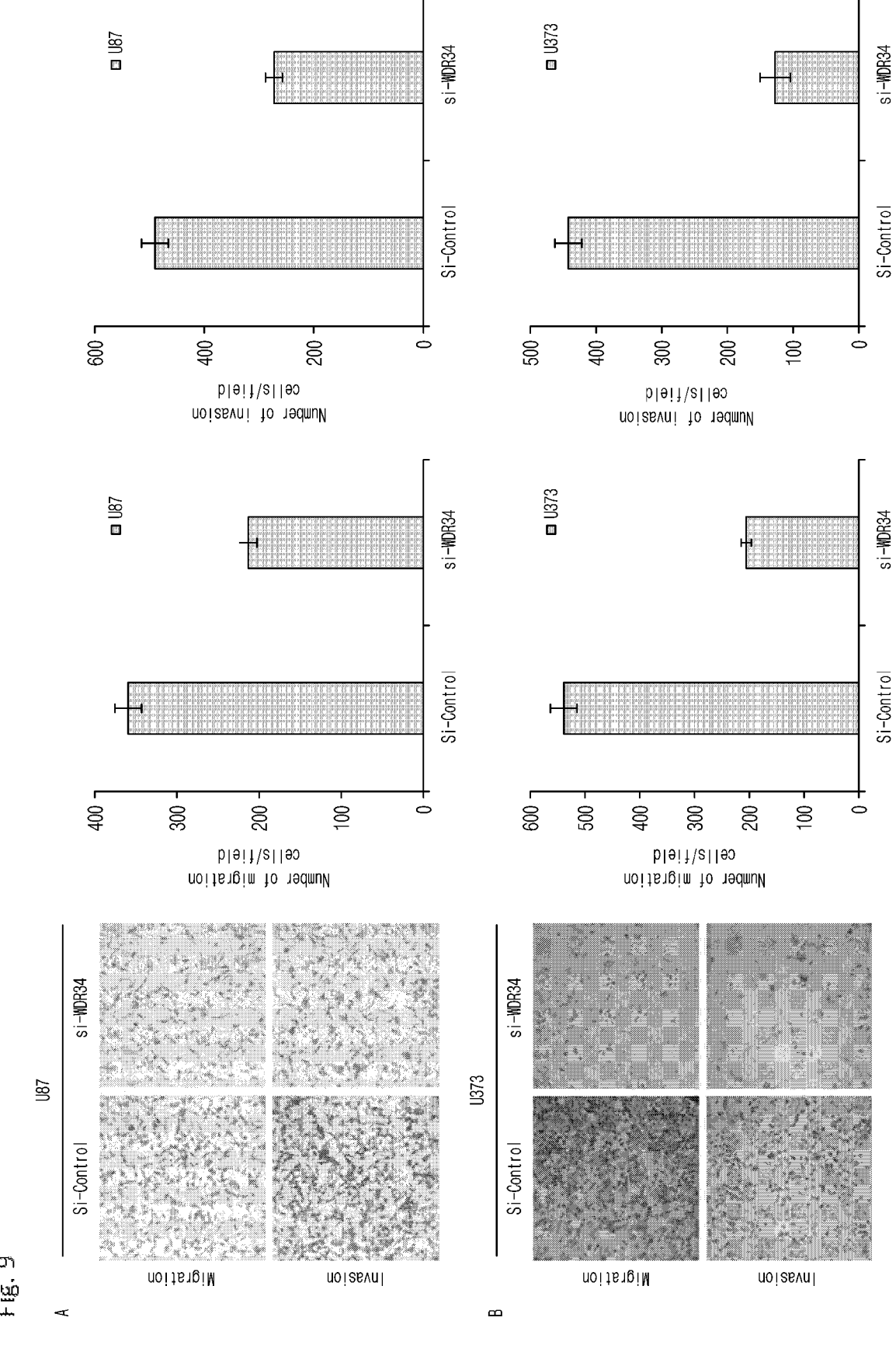

A and B of FIG. 9 show the invasion ability of cancer stem cells after treating brain cancer stem cells (U87-CD133+, U373-CD133+) with WDR34 siRNA, as a result of microscopic observation and the number of migrated cells.

Figure 10:
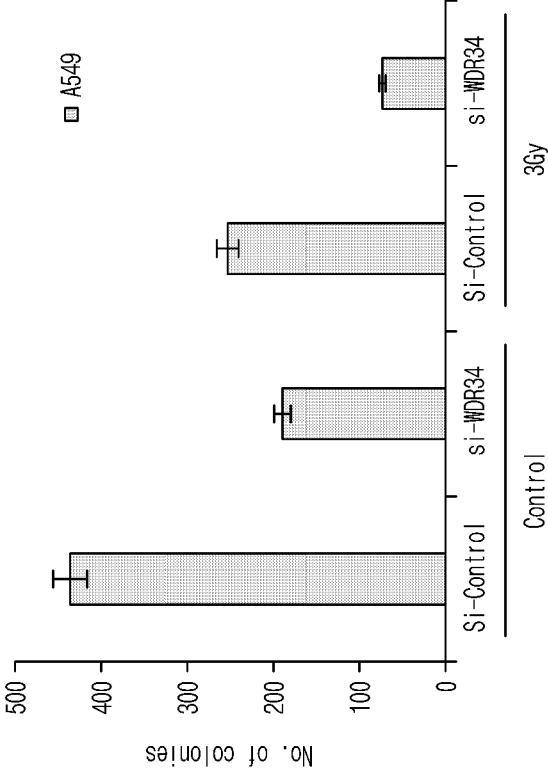
Figure 10:
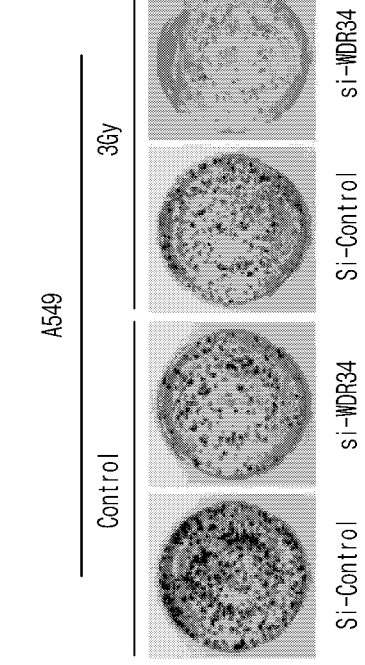

FIG. 10 is the results of treating lung cancer cells (A549) with WDR34 siRNA and then checking the sensitivity of the lung cancer cells to radiation through a colony formation method.

Figure 11:
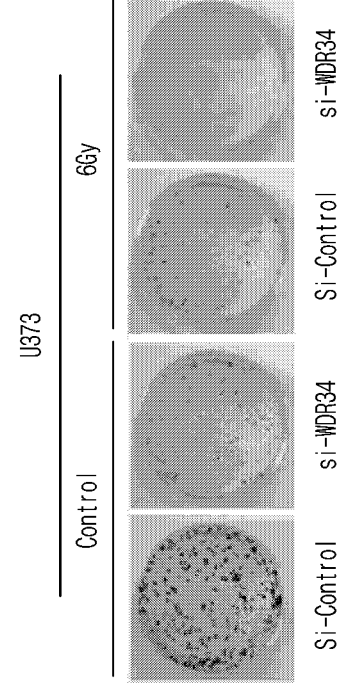
Figure 11:
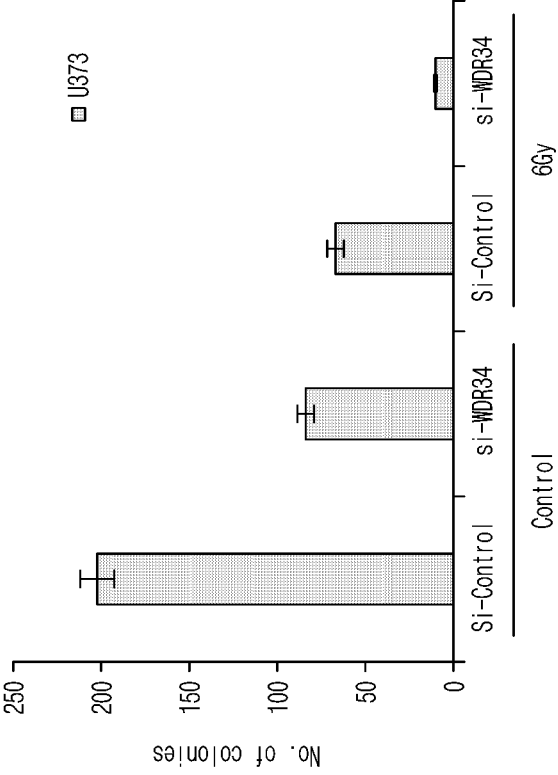

FIG. 11 is the results of treating brain cancer cells (U373) with WDR34 siRNA and then checking the sensitivity of the brain cancer cells to radiation through a colony formation method.

Figure 12:
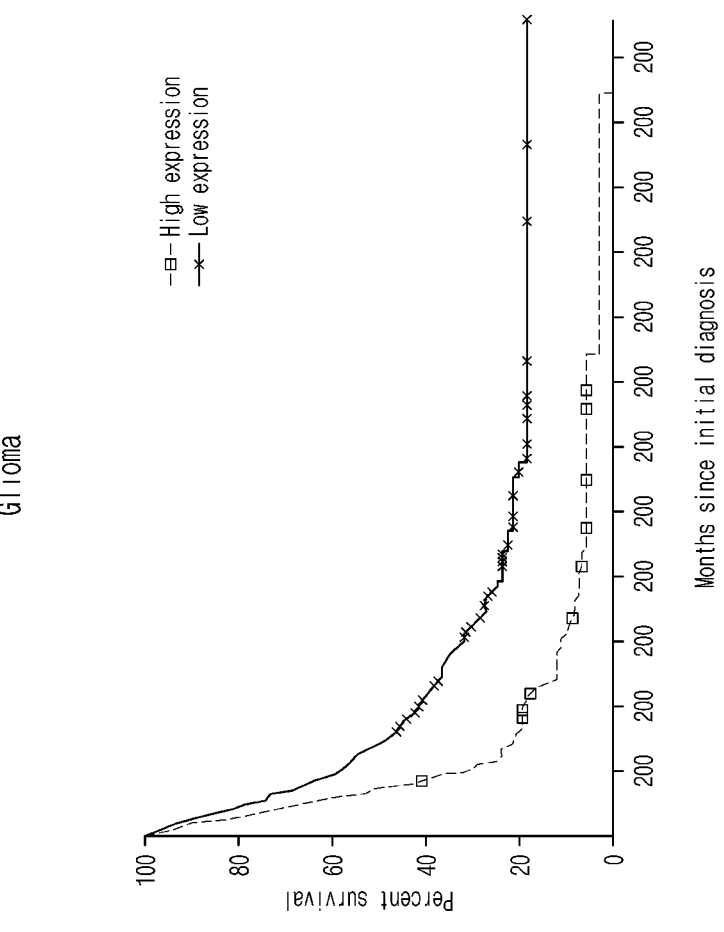
Figure 12:
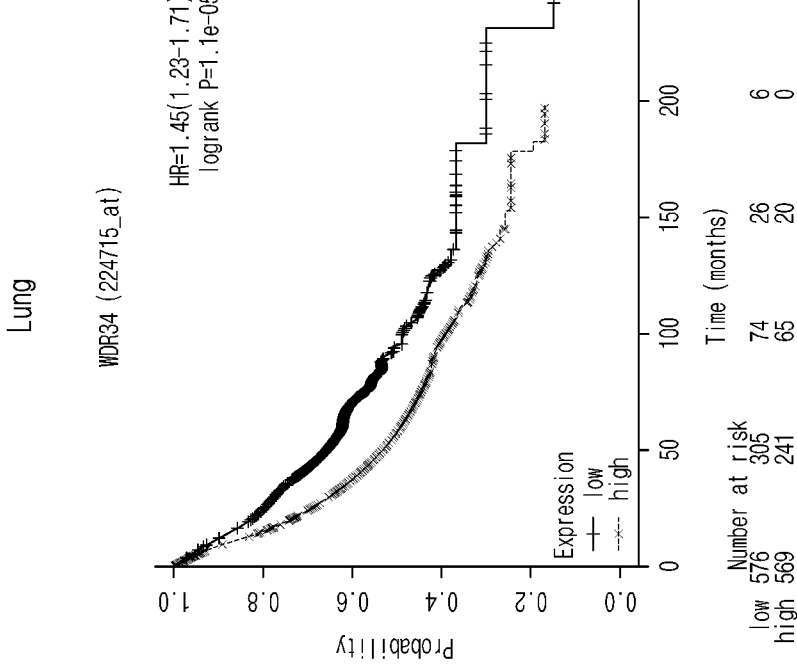

FIG. 12 shows a survival rate in a lung cancer patient group and a brain cancer patient group with high expression of WDR34 using the Kaplan-Meier curve.

4

MODE FOR CARRYING OUT THE INVENTION

Hereinafter, the present invention will be described in detail.

In one aspect, the present invention provides a composition for inhibiting the growth of cancer stem cells, the composition comprising a WD repeat domain 34 (WDR34) inhibitor as an active ingredient.

The term 'cancer stem cell (CSC)' in the present invention refers to an undifferentiated cell having the ability to differentiate into various cancer cells. Cancer stem cells are present in a ratio of about 1% to 2% in malignant tumor tissue, have self-replication ability and pluripotency, which are properties of normal stem cells, but have abnormal self-regulatory functions, and thus the number of cells increases due to cell division activation, and cancer stem cells differentiate themselves into malignant tumor cells. It is known that due to such properties of cancer stem cells, general cancer cells are removed through an anticancer treatment, but cancer stem cells survive, and cancer recurrence and metastasis are caused by some of the surviving cancer stem cells.

Specifically, the cancer stem cell according to the present invention may be cells sorted by one cancer stem cell marker selected from the group consisting of aldehyde dehydrogenase 1 (ALDH1), prominin-1 (CD133; AC122), and hyaluronate receptor (CD44; pglycoprotein 1), and specifically, may be cancer cells in which the marker gene is overexpressed or the activity of the marker protein is positive.

The 'WD repeat domain 34 (WDR34)' in the present specification is a member of the WD repeat protein family, and is involved in various cellular processes, including cell cycle progression, signal transduction, apoptosis, and gene regulation.

In the present invention, it was confirmed that WDR34 is overexpressed in cancer cells including cancer stem cells, WDR34 regulation can inhibit the growth and metastasis of cancer stem cells, and in particular, and an excellent anticancer effect can be achieved by killing a cancer cell group including cancer stem cells with high resistance to an anticancer treatment.

In one specific embodiment of the present invention, it was confirmed that cancer cells were classified into cancer stem cells and normal cancer cells, and WDR34 was expressed at a high level in the classified cancer stem cells.

In one specific embodiment of the present invention, it was confirmed that when WDR34 was inhibited through a treatment with siRNA, the size and number of cancer stem cells were reduced compared to the control group, and the adhesion ability of cancer cells, including cancer stem cells, to the extracellular matrix was significantly degraded.

In one specific embodiment of the present invention, it was confirmed that when WDR34 was inhibited through a treatment with siRNA in order to confirm the correlation of WDR34 with the renewal ability of cancer stem cells, the size and number of self-renewed cancer stem cells were smaller compared to the control group.

In one specific embodiment of the present invention, it was confirmed that when WDR34 was inhibited in order to confirm the correlation of WDR34 with the change in metastasis of cells, that is, migration and invasion ability, the invasion ability and migration ability of the cancer stem cells were significantly degraded.

In one specific embodiment of the present invention, it was confirmed that when WDR34 was inhibited in order to confirm the correlation of WDR34 inhibition with the resistance to a radiation treatment, a small colony of cells surviving after irradiation with radiation was formed.

The term 'WDR34 inhibitor' in the present invention is used to collectively refer to all substances that reduce the expression or activity of WDR34, and specifically includes all formulations that reduce the expression level or activity of WDR34 by reducing the expression of WDR34 at the transcriptional level or interfering with the activity of WDR34, through a method such as acting directly on WDR34 or acting indirectly on a ligand thereof.

The WDR34 inhibitor can be used without limitation on the form thereof, such as a compound, a nucleic acid, a peptide, a virus, or a vector containing the nucleic acid, which can target WDR34 to inhibit the expression or activity of WDR34. The WDR34 inhibitor is not limited to these examples, but may be specifically an oligonucleotide which inhibits the expression of WDR34 mRNA, or an antibody, which inhibits the activity of WDR34 protein or a ligand protein for WDR34, or an antigen-binding fragment thereof, and more specifically, the oligonucleotide acting on WDR34 mRNA may be an antisense oligonucleotide, an aptamer, shRNA, or siRNA, which is specific for the WDR34 mRNA.

The term "antisense oligonucleotide" in the present invention is DNA, RNA, or a derivative thereof containing a nucleic acid sequence that is complementary to the sequence of specific mRNA, and the antisense oligonucleotide binds to a complementary sequence in mRNA and acts to inhibit the translation of mRNA into a protein. The antisense oligonucleotide sequence refers to a DNA or RNA sequence that is complementary to the WDR34 mRNA and capable of binding to the mRNA. The sequence can inhibit the essential activity for translation of the WDR34 mRNA, translocation into the cytoplasm, maturation, or all other overall biological functions. The length of the antisense oligonucleotide may be 6 to 100 bases, preferably 8 to 60 bases, and more preferably 10 to 40 bases. The antisense oligonucleotide can be synthesized in vitro by a conventional method and administered in vivo, or the antisense oligonucleotide can be synthesized in vivo. One example of synthesizing the antisense oligonucleotide in vitro is using RNA polymerase I. One example of allowing antisense RNA to be synthesized in vivo is allowing antisense RNA to be transcribed by using a vector with the origin of a multiple cloning site (MCS) in the opposite direction. It is preferable that the antisense RNA is not translated into a peptide sequence by allowing a translation stop codon to be present in the sequence thereof. The design of the antisense oligonucleotide, which can be used in the present invention, can be made according to a method known in the art with reference to the base sequence of WDR34.

The term "aptamer" in the present invention is a single-stranded oligonucleotide, and refers to a nucleic acid molecule having a size of about 20 to 60 nucleotides and having binding activity to a predetermined target molecule. The aptamer has various three-dimensional structures according to the sequence, and can have high affinity with a specific substance, like an antigen-antibody reaction. The aptamer can inhibit the activity of a predetermined target molecule by binding to the predetermined target molecule. The aptamer according to the present invention may be RNA, DNA, a modified nucleic acid, or a mixture thereof, and may be in a linear or cyclic form. Preferably, the aptamer can play a role in inhibiting the activity of WDR34 by binding to WDR34. Such an aptamer can be produced from the sequence of WDR34 by a person with ordinary skill in the art through a known method.

The term "siRNA" or "shRNA" in the present invention is a nucleic acid molecule capable of mediating RNA interference or gene silencing, and can suppress the expression of a target gene and is thus used in an efficient gene knockdown method or gene therapy method. shRNA is a single-stranded oligonucleotide in which a hairpin structure is formed through binding between complementary sequences, and the shRNA is cleaved by a dicer in vivo to become siRNA, which is a double-stranded oligonucleotide and is a small RNA fragment having a size of 21 to 25 nucleotides, and can specifically bind to mRNA having a complementary sequence to thereby inhibit the expression thereof. Therefore, which means of shRNA and siRNA to be used can be determined through the selection of a person with ordinary skill in the art, and if mRNA sequences targeted by shRNA and siRNA are the same, a similar expression reduction effect can be expected. For the purposes of the present invention, shRNA and siRNA can inhibit WDR34 by specifically acting on WDR34 and cleaving WDR34 mRNA molecules to induce an RNA interference (RNAi) phenomenon. siRNA can be chemically or enzymologically synthesized. A method for producing siRNA is not particularly limited, and methods known in the art can be used. For example, there are a method for directly chemically synthesizing siRNA, a method for synthesizing siRNA using in vitro transcription, a method for cleaving, using an enzyme, long double-stranded RNA synthesized by in vitro transcription, an expression method through intracellular delivery of an shRNA-expressing plasmid or a viral vector, an expression method through intracellular delivery of a polymerase chain reaction (PCR)-induced siRNA expression cassette, and the like, but the method for producing siRNA is not limited to these examples.

Specifically, siRNA for WDR34 according to the present invention may be the oligonucleotide of SEQ ID NO: 2 or an oligonucleotide having the sequence of SEQ ID NO: 3, but is not limited thereto.

Moreover, the oligonucleotide of SEQ ID NO: 2 or SEQ ID NO: 3 includes an oligonucleotide comprising substantially the same base sequence as that of the oligonucleotide of SEQ ID NO: 2 or SEQ ID NO: 3. The oligonucleotide comprising substantially the same base sequence refers to an oligonucleotide comprising a base sequence having a sequence homology of 75% or greater, 80% or greater, 85% or greater, 90% or greater, or 95% or greater to the base sequence of SEQ ID NO: 2 or SEQ ID NO: 3.

The term "antibody" in the present invention refers to a substance that reacts to an antigen, which is an external substance, when the antigen invades while circulating in blood or lymph in the immune system of a living body, and is a globulin-based protein formed in lymphoid tissue and also called an immunoglobulin. The antibody is a protein produced by B cells and flowing into body fluids, and specifically binds to an antigen, one antibody molecule has two heavy chains and two light chains, and each heavy chain and each light chain have a variable region at an N-terminal end thereof. Each variable region consists of three complementarity determining regions (CDRs) and four framework regions (FRs), and the complementarity determining regions determine the antigen-binding specificity of an antibody, and are present as relatively short peptide sequences maintained by framework regions of the variable region.

For the purposes of the present invention, the antibody may be an antibody capable of inhibiting the activity of WDR34 by binding to WDR34 or a ligand protein of WDR34.

The term "ligand" in the present invention refers to a substance that forms a complex with a biomolecule to bring about a biological reaction, and the "ligand protein of WDR34" or "ligand protein for WDR34" may be a protein that binds to WDR34 to thereby activate WDR34 or increase the activity of WDR34.

As described above, the WDR34 inhibitors can inhibit the growth of cancer stem cells by inhibiting the transformation of cancer cells into cancer stem cells (formation of cancer stem cells) and the self-renewal, invasion, and migration ability of the cancer stem cells.

In the composition for inhibiting the growth of cancer stem cells according to the present invention, cancer of the cancer stem cells may be one or more selected from the group consisting of lung cancer, gastric cancer, ovarian cancer, cervical cancer, breast cancer, pancreatic cancer, colorectal cancer, colon cancer, esophageal cancer, skin cancer, thyroid cancer, kidney cancer, liver cancer, head and neck cancer, bladder cancer, prostate cancer, hematologic cancer, multiple myeloma, acute myeloid leukemia, malignant lymphoma, thymus cancer, osteosarcoma, fibrous tumor, and brain cancer. Specifically, the cancer may be cancer having, as a marker factor for cancer stem cells, one selected from the group consisting of ALDH1, CD133, and CD44. For example, cancer having ALDH1 as a marker factor for cancer stem cells may be breast cancer or lung cancer, cancer having CD133 as a marker factor for cancer stem cells may be brain cancer, colorectal cancer, pancreatic cancer, or lung cancer, and cancer having CD44 as a marker factor for cancer stem cells may be breast cancer or pancreatic cancer.

In another aspect, the present invention provides a method for inhibiting the growth of cancer stem cells, the method comprising a step for treating cancer stem cells with a WD repeat domain 34 (WDR34) inhibitor.

In another aspect, the present invention provides a method for preventing or treating cancer, administering a composition comprising a WDR34 inhibitor as an active ingredient, to a subject in need thereof.

In the method for inhibiting the growth of cancer stem cells or preventing or treating cancer according to the present invention, the details of the WDR34 and the cancer stem cells are as described above.

In still another aspect, the present invention provides a composition for preventing or treating cancer, the composition comprising a WD repeat domain 34 (WDR34) inhibitor as an active ingredient.

In one exemplary embodiment of the present invention, the cancer may be 'cancer having cancer stem cell properties'.

The term 'cancer having cancer stem cell properties' in the present invention refers to cancer with a high proportion of cancer stem cells in a cell group constituting cancer. Considering that the proportion of cancer stem cells in general cancer cells is about 1% or greater and less than 5%, for example, a case in which the proportion of cancer stem cells in a cell group constituting cancer is 5% or greater, 10% or greater, 30% or greater, 50% or greater, or 70% or greater can be defined as 'cancer having cancer stem cell properties', and the cancer having cancer stem cell properties can be characterized by showing resistance to anticancer treatments, which targets existing cancer cells, and having a poor prognosis for the anticancer treatments.

Specifically, the 'cancer having cancer stem cell properties' in the present invention may be anticancer immune-resistant cancer, resistant cancer, recurrent cancer, or metastatic cancer.

The "primary cancer" in the present specification refers to typical cancer, the "immune-resistant cancer" refers to cancer that has acquired resistance to anticancer immunotherapy, and the anticancer immunotherapy refers to the integration of all systems that induce an immune response to a cancer-specific antigen or a cancer-related antigen and eliminate cancer cells by cancer-specific toxic immune cells. The "recurrent cancer" refers to cancer that has recurred after a typical cancer treatment, and the "resistant cancer" refers to cancer that is resistant to the aforementioned cancer treatment. Here, the typical cancer treatment includes, for example, surgery, chemotherapy, a radiation treatment, a hormone treatment, a biological therapy, immunotherapy, and the like. Moreover, the "cancer metastasis or metastatic cancer" in the present specification means that primary cancer or recurrent cancer occurring in a specific site is metastasized to another site.

The type of the cancer may include lung cancer, gastric cancer, ovarian cancer, cervical cancer, breast cancer, pancreatic cancer, colorectal cancer, colon cancer, esophageal cancer, skin cancer, thyroid cancer, kidney cancer, liver cancer, head and neck cancer, bladder cancer, prostate cancer, hematologic cancer, multiple myeloma, acute myeloid leukemia, malignant lymphoma, thymus cancer, osteosarcoma, fibrous tumor, brain cancer, and the like.

In one exemplary embodiment of the present invention, the cancer may be WDR34-overexpressing cancer and more specifically WDR34-overexpressing lung cancer or brain cancer.

The WDR34 protein according to the present invention exhibits resistance to an anticancer drug and radiation, and is highly expressed in cancer stem cells having high metastatic properties, and thus can be used for the treatment of recurrent cancer, resistant cancer, or cancer metastasis as well as the recurrence and metastasis of anticancer immune-resistant cancer, by administering an inhibitor that inhibits the expression or activity of the protein or genes of the protein.

The WDR34 protein-overexpressing cancer according to the present invention is cancer, in which a cancer stem cell marker such as ALDH1, CD133, or CD44 is overexpressed or the activity of the protein is positive, and may be cancer having a relatively higher ratio of cancer stem cells compared to normal cancer.

In the composition for preventing or treating cancer according to the present invention, the prevention or treatment of cancer includes the prevention, inhibition, or alleviation of cancer chemoresistance, cancer recurrence, or cancer metastasis during or after a cancer treatment.

In one exemplary embodiment, the present inventors distinguished and sorted ALDH1-activated cells and ALDH1-inactivated cells, and confirmed that the expression levels of WDR34 were increased in the ALDH1-activated cells. Moreover, in one exemplary embodiment, the present inventors confirmed that cancer stem cells having ALDH1 activity were a major factor in cancer growth, from the decrease in the self-renewal ability, migration ability, and invasion ability of lung cancer stem cells when ALDH1-activated lung cancer cells were treated with a WDR34 inhibitor.

In the composition for preventing or treating cancer according to the present invention, the details of the WDR34 and the WDR34 inhibitor are as described above.

When the composition for preventing or treating cancer of the present application is used as a pharmaceutical composition, the pharmaceutical composition may further contain a pharmaceutically acceptable carrier or additive, in addition to the WDR34 inhibitor.

The 'pharmaceutically acceptable' means that the substance does not inhibit the activity of the active ingredient and does not have toxicity beyond what an application (prescription) target is adaptable to, and the 'carrier' is defined as a compound that facilitates the addition of a compound into cells or tissue.

The pharmaceutical composition according to the present invention may be administered alone or in the form of a mixture with any convenient carrier or the like, and such an administration dosage form may be a single-administration or repeated-administration dosage form. The pharmaceutical composition may be a solid formulation or a liquid formulation. The solid formulation includes a powdered drug, a granule, a tablet, a capsule, a suppository, and the like, but is not limited to these examples. The solid formulation may contain a carrier, a flavoring agent, a binding agent, a preservative, a disintegrating agent, a lubricant, a filler, and the like, but is not limited thereto. The liquid formulation includes water, a solution agent such as a propylene glycol solution, a suspension, an emulsion, and the like, but is not limited to these examples, and can be produced by adding an appropriate colorant, flavoring agent, stabilizing agent, or viscosity-increasing agent. For example, the powdered drug can be produced by simply mixing a tri-hydroxy derivative of a polyunsaturated fatty acid, which is the active ingredient of the present invention, and an appropriate pharmaceutically acceptable carrier such as lactose, starch, or microcrystalline cellulose. The granule can be produced by mixing the tri-hydroxy derivative of the polyunsaturated fatty acid of the present invention, an appropriate pharmaceutically acceptable carrier, and an appropriate pharmaceutically acceptable binding agent such as polyvinylpyrrolidone and hydroxypropyl cellulose, and then using a wet granulation method using a solvent such as water, ethanol, or isopropanol, or a dry granulation method using a compressive force. Moreover, the tablet can be produced by mixing the aforementioned granule and an appropriate pharmaceutically acceptable lubricant such as magnesium stearate, and then tableting the mixture using a tableting machine.

The pharmaceutical composition may be administered as an oral agent, an injection (for example, an intramuscular injection, an intraperitoneal injection, an intravenous injection, an infusion, a subcutaneous injection, and an implant), an inhalant, a nasal administration agent, a vaginal agent, a rectal administration agent, a sublingual agent, a transdermal agent, a topical agent, or the like, depending on the disease to be treated and the conditions of a subject, but is not limited thereto. The pharmaceutical composition can be formulated into an appropriate administration unit dosage form, which is typically used and non-toxic and contains a pharmaceutically acceptable carrier, additive, and vehicle, according to the route of administration.

The pharmaceutical composition may be administered in an amount of about 0.0001 mg/kg to about 10 g/kg daily, and may be administered in a daily dosage of about 0.001 mg/kg to about 1 g/kg. However, the dosage may vary depending on the degree of purification of the mixture, the conditions (age, sex, body weight, and the like) of a patient, the severity of the condition being treated, and the like. The total daily dose may be administered in several divided doses during the day for convenience as needed.

In still another aspect, the present invention provides a method for screening a substance for inhibiting cancer recurrence or cancer metastasis, the method comprising:

treating a WDR34-expressing cell line with a candidate substance; measuring the expression or activity level of WDR34 in the cell line; and sorting a substance with which the expression or activity level of WDR34 is reduced compared to a control group that is not treated with a candidate substance.

The cancer may be lung cancer, gastric cancer, ovarian cancer, cervical cancer, breast cancer, pancreatic cancer, colorectal cancer, colon cancer, esophageal cancer, skin cancer, thyroid cancer, kidney cancer, liver cancer, head and neck cancer, bladder cancer, prostate cancer, hematologic cancer, multiple myeloma, acute myeloid leukemia, malignant lymphoma, thymus cancer, osteosarcoma, fibrous tumor, brain cancer, and the like, specifically WDR34-overexpressing cancer, and more specifically WDR34-over-expressing lung cancer or brain cancer.

The WDR34-expressing cell line may be a human lung cancer cell line or a human brain cancer cell line.

In one specific embodiment of the present invention, it was confirmed that when the expression of WDR34 was inhibited using siRNA in WDR34-overexpressed cancer cells, the expression of ALDH1, CD44, and Nanog serving as markers for cancer stem cells was reduced, and thus candidate substances for various types of cancer metastasis inhibitors and cancer stem cell growth inhibitors can be screened by sorting candidate substances with which the expression or activity level of WDR34 is reduced.

In still another aspect, the present invention provides a composition for inhibiting cancer recurrence or cancer metastasis, the composition comprising a WD repeat domain 34 (WDR34) inhibitor as an active ingredient.

The composition according to the present invention comprises a WDR34 inhibitor as an active ingredient for inhibiting cancer recurrence or cancer metastasis. The details of the WDR34 and the WDR34 inhibitor are as described above.

The cancer may be lung cancer, gastric cancer, ovarian cancer, cervical cancer, breast cancer, pancreatic cancer, colorectal cancer, colon cancer, esophageal cancer, skin cancer, thyroid cancer, kidney cancer, liver cancer, head and neck cancer, bladder cancer, prostate cancer, hematologic cancer, multiple myeloma, acute myeloid leukemia, malignant lymphoma, thymus cancer, osteosarcoma, fibrous tumor, brain cancer, and the like, specifically WDR34-overexpressing cancer, and more specifically WDR34-over-expressing lung cancer or brain cancer.

In one specific embodiment of the present invention, it was confirmed that when WDR34 was inhibited through a treatment with siRNA in a WDR34-overexpressing lung cancer cell line or brain cancer cell line, the formation, self-renewal, invasion, and migration ability of cancer stem cells, which play a key role in cancer recurrence or metastasis, were degraded, and thus cancer recurrence or cancer metastasis can be prevented or inhibited through a treatment with a WDR34 expression or activity inhibitor.

In still another aspect, the present invention provides a composition for assisting a radiation anticancer treatment, the composition comprising a WD repeat domain 34 (WDR34) inhibitor as an active ingredient.

The composition according to the present invention comprises a WDR34 inhibitor as an active ingredient for improving the sensitivity of cancer cells, including cancer stem cells, to radiation. The details of the WDR34 and the WDR34 inhibitor are as described above.

The composition according to the present invention may be administered before or together with the radiation to a subject in need of a radiation anticancer treatment.

Moreover, the cancer cells, including cancer stem cells, may be cancer cells having low sensitivity to radiation, that is, cancer cells having high resistance to a radiation treatment, and may be substantially insensitive to radiation, and thus an anticancer treatment through irradiation with radiation may be impossible.

The cancer stem cells may be undifferentiated cells having the ability to differentiate into various cancer cells, and specifically cancer cells in which WDR34, ALDH1, and/or CD133 is expressed or the activity thereof is positive. The cancer stem cells in the present invention may have characteristics that even by irradiation with radiation, the cell proliferation is not inhibited, the self-renewal ability is not degraded, and the migration and invasion ability is not inhibited.

The anticancer may induce proliferation inhibition, metastasis and invasion inhibition, and cell death of cancer cells, including cancer stem cells, through irradiation with radiation, a surgical procedure, chemotherapy, or the like. The anticancer in the present invention may be the administration of the WDR34 inhibitor in combination with irradiation with radiation. When the WDR34 inhibitor is administered in combination with irradiation with radiation as described above, the sensitivity of cancer cells, including cancer stem cells, to radiation is improved by the WDR34 inhibitor, and thus the anticancer therapeutic effect by irradiation with radiation can be maximized, and cancer recurrence and metastasis can be prevented.

The cancer may be lung cancer, gastric cancer, ovarian cancer, cervical cancer, breast cancer, pancreatic cancer, colorectal cancer, colon cancer, esophageal cancer, skin cancer, thyroid cancer, kidney cancer, liver cancer, head and neck cancer, bladder cancer, prostate cancer, hematologic cancer, multiple myeloma, acute myeloid leukemia, malignant lymphoma, thymus cancer, osteosarcoma, fibrous tumor, brain cancer, and the like, specifically WDR34-overexpressing cancer, and more specifically WDR34-overexpressing lung cancer or brain cancer.

Hereinafter, the present invention will be described in detail with reference to Examples and Experimental Examples.

However, the following Examples and Experimental Examples specifically illustrate the present invention, and the contents of the present invention are not limited by e following Examples and Experimental Examples.

EXAMPLE 1

Checking of Expression Level of WDR34 Genes in Cancer Stem Cells
<1-1> Cell Culture and Formation of Cancer Stem Cells The human lung cancer cell line A549 obtained from American Type Culture Collection (ATCC, USA) and the human brain cancer cell lines U87 and U373 obtained from Korean Cell Line Bank were cultured under conditions of 37° C. and humidified 5% $CO_2$. The A549 cells and the U373 cells were cultured in an RPMI medium supplemented with 10% fetal bovine serum and streptomycin (100 g/ml). The U87 cells were cultured in a DMEM medium supplemented with 10% fetal bovine serum and streptomycin (100 g/ml).

Next, the lung cancer cells (A549) and brain cancer cells (U87, U373) cultured as described above were re-cultured in a DMEM/F12 medium containing bFGF (20 ng/ml), bEGF (20 ng/ml), and B27 stem cell supplement (1×) to transform the cells into cancer stem cells.

<1-2> Isolation of Cancer Stem Cells and Checking of WDR34 Overexpression

The A549 cells cultured in Example <1-1> were classified into ALDH1-positive cells (A549-ALDH1$^+$) and ALDH1-negative cells (A549-ALDH1$^-$), through the activity of ALDH1 serving as a marker protein for lung cancer stem cells. Moreover, the U87 and U373 cells were classified into CD133-positive cells (U87-CD133$^+$, U373-CD133$^+$) and CD133-negative cells (U87-CD133, U373-CD133), through the activity of CD133 serving as a marker protein for brain cancer stem cells.

Next, gene differences between the ALDH1-positive cells and the ALDH1-negative cells, and between the CD133-positive cells and the CD133-negative cells were comparatively analyzed by performing gene analysis using a microarray.

Figure 1:
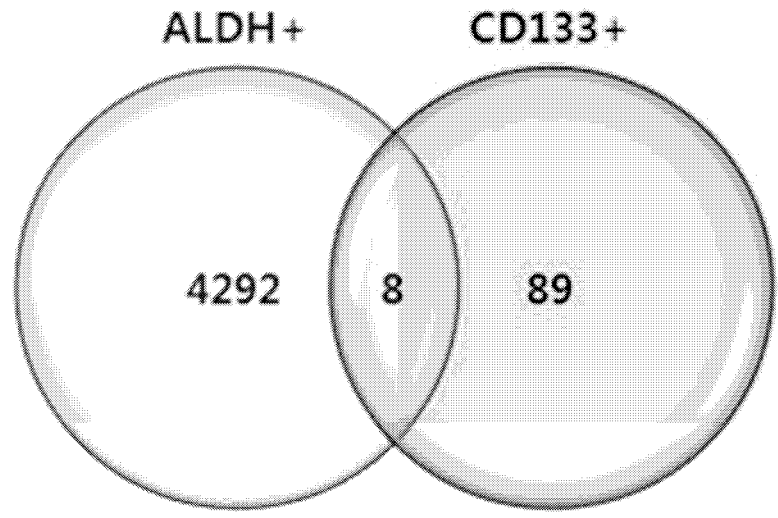
FIG. 1 shows genes that are commonly overexpressed in an ALDH-positive cell and a CD133-positive cell, and is a Venn diagram showing that the number of genes with at least two-fold higher expression in the ALDH+ cell was 4,300, the number of genes with at least two-fold higher expression in the CD133+ cell was 97, and 8 genes were sorted as an intersection thereof.

As a result, it was confirmed that the expression levels of WDR34 in the ALDH1-positive cells (A549-ALDH1$^+$) and the CD133-positive cells (U87-CD133$^+$, U373-CD133$^+$) were significantly increased, respectively, compared to the ALDH1-negative cells and the CD133-negative cells. Moreover, it was confirmed that WDR34 was highly expressed in both the lung cancer stem cells and the brain cancer stem cells (FIG. 1).

The results indicate that WDR34 genes are related to lung cancer stem cells and brain cancer stem cells. In order to specifically check the effect of WDR34 on cancer stem cells, the following experiments were conducted.

EXAMPLE 2

Checking of Inhibitory Effect on Transformation of Cancer Cells into Cancer Stem Cells
<2-1> Checking of Size (Sphere Formation) of Lung Cancer Stem Cells and Change in Expression of Transcription Factor When cancer cells are treated with a cancer stem cell culture solution, the cancer cells, which have adhered and grown, become spherical and show a non-adhesion form. This is a method typically used in cancer stem cell research, and is a phenomenon in which cancer cells are transformed into cancer stem cells. The A549 cells, which are human lung cancer cells, were treated with siRNA targeting WDR34, and the size of the cancer stem cells and a change in the expression of a transcription factor were checked.

Specifically, $5 \times 10^5$ cells/ml of A549 as a human lung cancer cell line was dispensed into a 100-mm dish, and sufficiently cultured. Thereafter, genes were directly inhibited through a treatment with 0.17 μg/mL of WDR34 siRNA, the cells were then cultured for 9 days in a cancer stem cell culture medium [DMEM/F12 containing bFGF (20 ng/ml), bEGF (20 ng/ml), and B27 stem cell supplement (1×)], and the size and number of the cancer stem cells were observed with a microscope. Moreover, changes in the expression of transcription factors involved in the maintenance of pluripotency of cancer stem cells were checked using a PCR. As the siRNA, siRNA sequences, which are 5'-GGA GCA CGC UUA AGU CCU U-3' (SEQ ID NO: 2) and 5'-AAG GAC UUA AGC GUG CUC C-3' (SEQ ID NO: 3), for WDR34 genes were customized by BIONEER CORPORATION and used.

Figure 2:
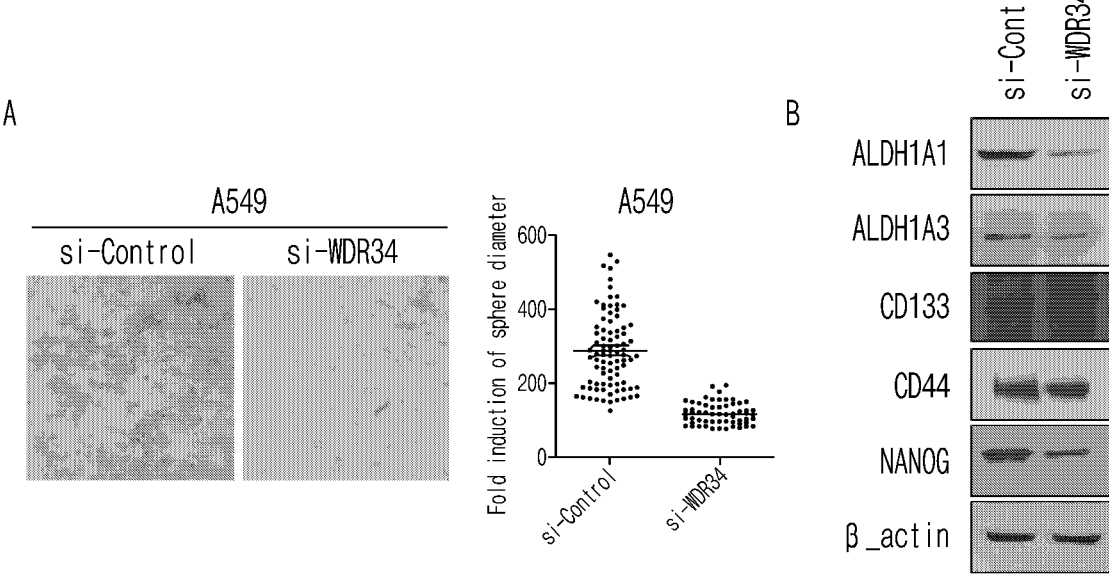
FIG. 2 is the results of treating lung cancer cells (A549) with WDR34 siRNA and then checking the cancer stem cell formation ability of the lung cancer cells, A is the results of analyzing the size and number of cancer stem cells, and B is the results of checking, through PCR, the changes in the expression levels of ALDH1 and CD44, which are marker proteins of the lung cancer stem cells, and NANOG, which is a transcription factor of cancer stem cells, depending on the presence or absence of a siRNA treatment.

As a result, as shown in A of FIG. 2, it was confirmed that in the experimental group treated with Si-WDR34, the cancer stem cell formation ability was significantly degraded and the number of the cancer stem cells was also reduced, compared to the control group (Si-Control) that was not treated with Si-WDR34.

Furthermore, as shown in B of FIG. 2, it was confirmed that in the experimental group treated with Si-WDR34, the expression of ALDH1, CD133, and CD44 serving as marker proteins for lung cancer stem cells was reduced, and the expression of NANOG involved in the maintenance of pluripotency of cancer stem cells was reduced, compared to the control group (Si-Control) that was not treated with Si-WDR34.

Combining these results, it can be seen that WDR34 is involved in the formation of cancer stem cells, and can regulate transcription factors important for maintaining of pluripotency of cancer stem cells to inhibit the formation of the cancer stem cells.

<2-2> Checking of Size (Sphere Formation) of Brain Cancer Stem Cells and Change in Expression of Transcription Factor The U87 and U373 cells as human brain cancer cells were treated with siRNA in the same manner as in Example <2-1> to directly inhibit WDR34 genes, and then the size and number of the cancer stem cells were checked, and changes in the expression of marker proteins and transcription factors were checked through Western blot.

Figure 3:
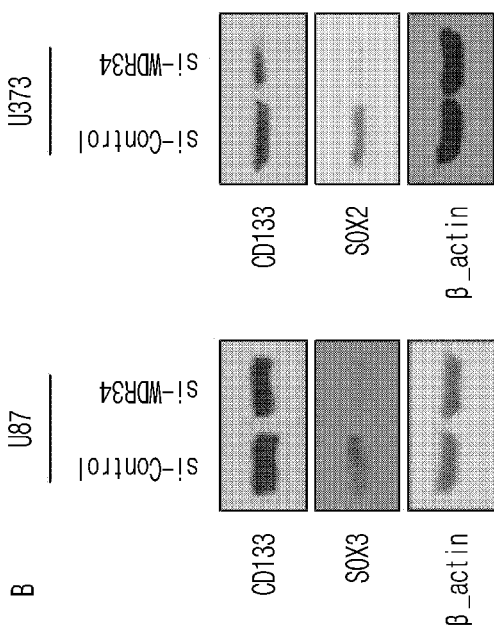
FIG. 3 is the results of treating brain cancer cells (U87, U373) with WDR34 siRNA and then checking the cancer stem cell formation ability of the brain cancer cells, and the results of analyzing the size and number of cancer stem cells.
Figure 3:
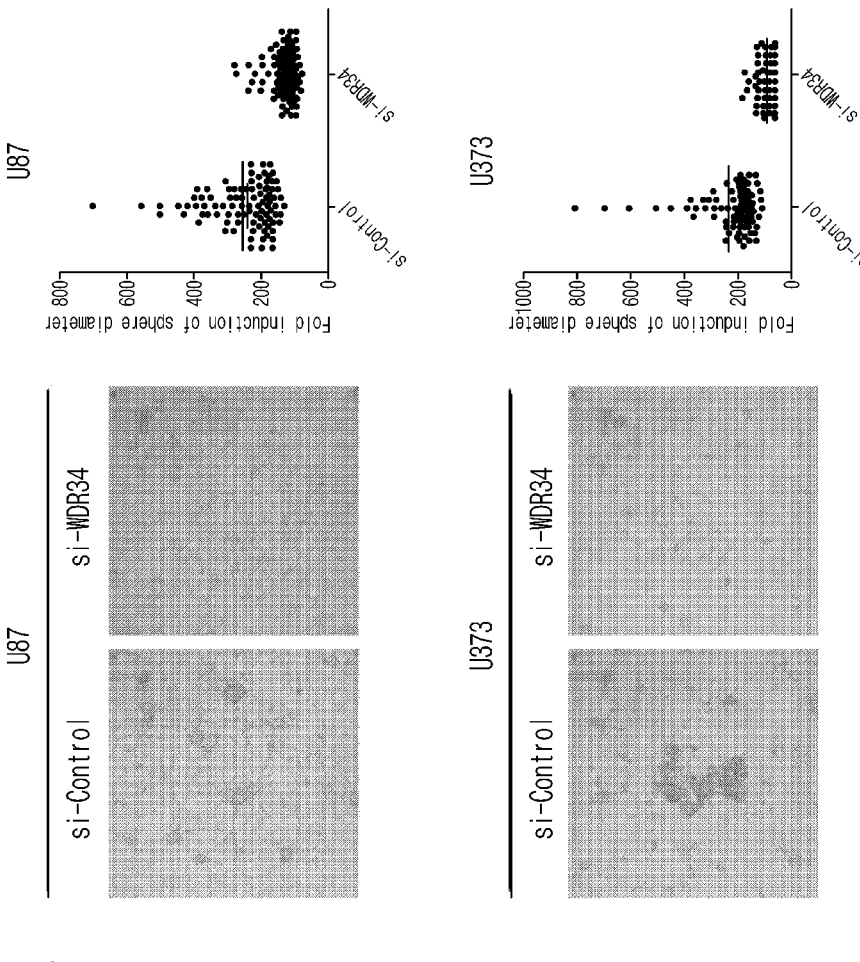

As a result, as shown in A of FIG. 3, it was confirmed that in the experimental group treated with Si-WDR34, cancer stem cells having a spherical shape and showing a non-adhesion form were less formed, compared to the control group (Si-Control) that was not treated with Si-WDR34. Moreover, as shown in B of FIG. 3, it was confirmed that in the experimental group treated with Si-WDR34, the expression levels of CD133 serving as a marker protein for brain cancer stem cells and SOX2 serving as a transcription factor were reduced, compared to the control group (Si-Control) that was not treated with Si-WDR34.

The results indicate that WDR34 is an important factor that regulates the formation of cancer stem cells not only in lung cancer cells but also in brain cancer cells.

EXAMPLE 3

Checking of Inhibitory Effect on Self-Renewal Ability of Cancer Stem Cells

<3-1> Checking of Inhibitory Effect on Self-Renewal Ability of Lung Cancer Stem Cells Through Treatment with WDR34 siRNA A single cell assay was performed in order to measure self-renewal ability which is one of the main characteristics of cancer stem cells.

Specifically, the A549-ALDH1$^+$ cells were dispensed one by one into a 96-well plate, and sufficiently cultured. The A549-ALDH1$^+$ cells cultured as described above were treated with or without 0.17 μg/mL of WDR34 siRNA, and cultured for 2 weeks.

With regard to the A549-ALDH1$^+$ cancer stem cells which were treated with or without WDR34 siRNA, the number of the cells present in the plate was measured using a microscope.

Figure 4:
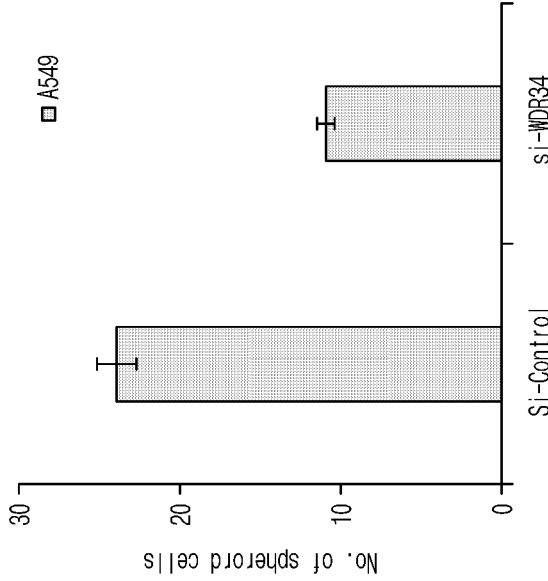
FIG. 4 is the results of treating lung cancer stem cells (A549-ALDH1+) with WDR34 siRNA and then checking the self-renewal ability of the cancer stem cells, A shows the results of microscopic observation, and B is a graph showing the measured number of cancer stem cells.
Figure 4:
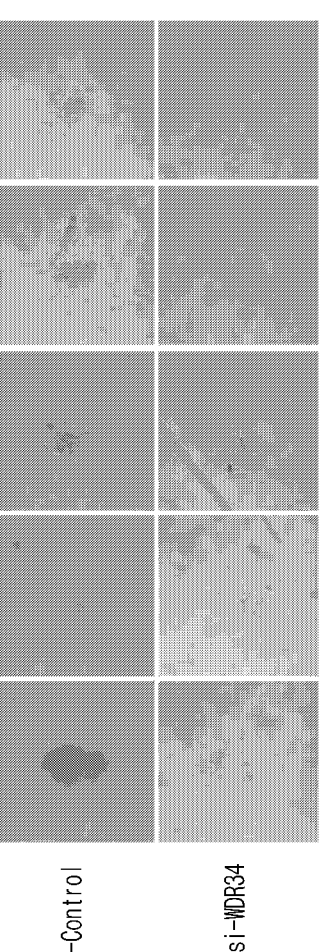

As a result, as shown in A of FIG. 4, it was confirmed that in the group treated with WDR34 siRNA, the degree of formation of cancer stem cells was significantly reduced compared to the control group.

From the result, it can be seen that inhibition of WDR34 can very effectively inhibit the self-renewal ability, which is an inherent property of cancer stem cells.

<3-2> Checking of Inhibitory Effect on Self-Renewal Ability of Brain Cancer Stem Cells Through Treatment with WDR34 siRNA In order to check, using the brain cancer stem cells (U87-CD133+, U373-133+), a change in the self-renewal ability of cancer stem cells through a treatment with WDR34 siRNA, an experiment was performed in the same manner as in Example <3-1>.

Figure 5:
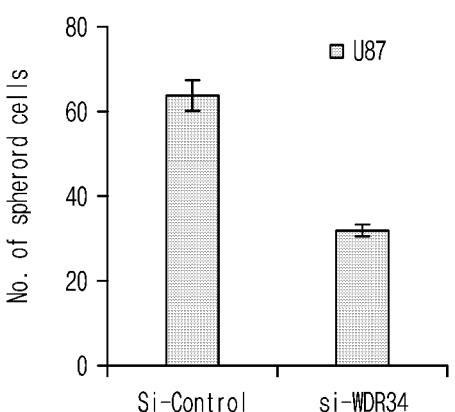
FIG. 5 is the results of treating brain cancer stem cells (U87-CD133+, U373-CD133+) with WDR34 siRNA and then checking the self-renewal ability of the cancer stem cells, and is a graph showing the measured number of cancer stem cells.
Figure 5:
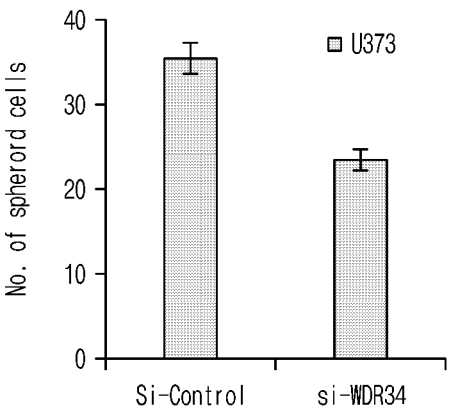

As a result, as shown in FIG. 5, it was confirmed that in both cases of the U87 cells and the U373 cells, the degree of cancer stem cell formation in the group treated with WDR34 siRNA was reduced. From the result, it can be seen that WDR34 genes are involved in the self-renewal ability of brain cancer stem cells.

EXAMPLE 4

Checking of Inhibitory Effect on Migration Ability of Cancer Stem Cells Through Scratch Analysis <4-1> Checking of Inhibitory Effect on Migration Ability of Lung Cancer Stem Cells Through Treatment with WDR34 siRNA Cancer stem cells are known to play a significant role in cell metastasis. The cell metastasis is closely related to cell movement. Therefore, in order to check the effect of WDR34 on the migration ability of cells, it was attempted to check, using the lung cancer stem cells isolated in Example 1-1, a change in the migration ability of cancer stem cells through a treatment with WDR34 siRNA.

Specifically, $2 \times 10^5$ cells/dish of the lung cancer stem cells (A549-ADH1+) were cultured in a 35-mm dish. In order to check the functions of WDR34, WDR34 was inhibited using siRNA and then cell migration ability was measured.

Figure 6:
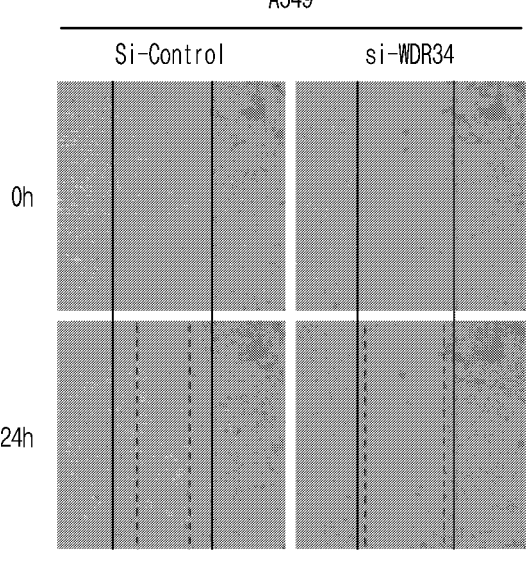
FIG. 6 shows the results of treating lung cancer stem cells (A549-ALDH1+) with WDR34 siRNA and then checking the migration ability of the cancer stem cells through scratch analysis.
Figure 6:
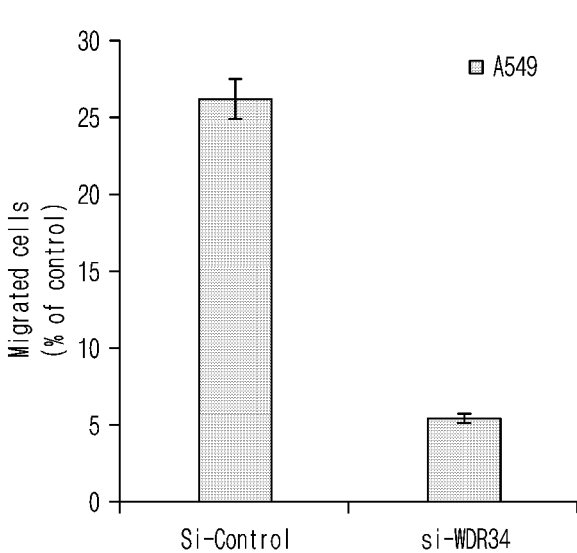

As a result, as shown in FIG. 6, lung cancer stem cells treated with siRNA to inhibit WDR34 were observed to have reduced migration compared to cells that were not treated at all.

From the result, it could be confirmed again that WDR34 regulates lung cancer stem cells to regulate the cell migration ability which is a characteristic of cancer stem cells.

<4-2> Checking of Inhibitory Effect on Migration Ability of Brain Cancer Stem Cells Through Treatment with WDR34 siRNA In order to check, using the brain cancer stem cells (U87-CD133+, U373-133+), a change in the migration ability of cancer stem cells through a treatment with WDR34 siRNA, an experiment was performed in the same manner as in Example <4-1>.

As a result, as shown in A and B of FIG. 7, brain cancer stem cells treated with siRNA to inhibit WDR34 were observed to have reduced migration compared to cells that were not treated at all.

From the result, it could be confirmed again that WDR34 regulates brain cancer stem cells to regulate the cell migration ability which is a characteristic of cancer stem cells.

EXAMPLE 5

Checking of Inhibitory Effect on Cancer Metastasis Through Invasion and Migration Analysis <5-1> Checking of Inhibitory Effect on Invasion and Migration Ability of Lung Cancer Stem Cells Through Treatment with WDR34 siRNA Cancer stem cells are involved in cancer recurrence through the self-renewal ability, and according to recent research results, it is known that cancer stem cells are the major cells that cause metastasis. In order to check the metastatic ability of cancer cells, it was attempted to check, using the lung cancer stem cells isolated in Example 1-1, a change in the invasion and migration ability of cancer stem cells through a treatment with WDR34 siRNA.

Specifically, the A549-ALDH1$^+$ cancer stem cells were isolated using trypsin, 5×10$^4$ cells were each suspended in 0.2 mL of a nutrient medium, 0.17 μg/mL of WDR34 siRNA was then placed in a Transwell upper chamber having a pore size of 8 μm, 800 μl of an RPMI1640 medium containing 10% fetal bovine serum was placed in a lower chamber, and the two chambers were combined. Thereafter, the cancer stem cells were cultured in an incubator at 37° C. under a condition of 5% $CO_2$ for 48 hours. Subsequently, the membrane of the upper chamber was wiped with a cotton swab, stained with a crystal violet solution, and observed with a microscope, and then the number of the cancer stem cells was measured to check the migration ability.

Moreover, the invasion analysis was performed in the same manner as in the process of checking the migration ability, except that a Transwell upper chamber coated with 10 mg/ml of a growth factor-reduced Matrigel (BD Biosciences, USA) was used.

As a result, as shown in FIG. 8, it was confirmed that when the treatment with WDR34 siRNA was performed, the number of cancer stem cells subjected to migration and invasion was significantly reduced compared to when the treatment with WDR34 siRNA was not performed.

<5-2> Checking of Inhibitory Effect on Invasion and Migration Ability of Brain Cancer Stem Cells Through Treatment with siRNA In order to check whether WDR34 is involved in the migration and penetration ability of cells also in the brain cancer cell lines (U87 and U373), the inhibitory effect on the invasion and migration ability of cancer stem cells through a treatment with a WDR34 inhibitor was checked in the same manner as in Example <5-1>, except that the brain cancer stem cells were used instead of the lung cancer stem cells.

As a result, as shown in A and B of FIG. 9, it was confirmed that when the treatment with siRNA was performed, the migration ability and invasion ability of cells, which are characteristics of cancer stem cells, were significantly reduced also in the case of brain cancer.

From the above results, it can be seen that the motility of cancer stem cells is regulated by WDR34, and the migration and invasion ability of cancer stem cells can be very effectively inhibited by inhibiting WDR34.

EXAMPLE 6

Checking of Effect of Improving Sensitivity of Cancer Cells to Radiation Through Colony Formation Method <6-1> Checking of Effect of Improving Sensitivity of Lung Cancer Cells to Radiation Through Treatment with WDR34 siRNA The lung cancer cells (A549) were applied by 5×10$^2$ each to a 35-mm dish, treated with or without 0.17 μg/mL of WDR34 siRNA one day after the application, and irradiated with radiation in a dose of 10 Gy. The treatment group irradiated with radiation was designated as an experimental group, and the group not irradiated with radiation was designated as a control group, and the cells of the experimental group and the control group were stained with a 0.5% crystal violet reagent for 10 minutes and washed several times with PBS, and then the number of colonies was measured to analyze the degree of colony formation.

As a result, as shown in FIG. 10, it was confirmed that when the treatment with siRNA was performed, colony formation was significantly reduced. Moreover, it was confirmed that in the group irradiated with radiation in a dose of 3 Gy, colony formation by the irradiation with radiation was reduced, but it was confirmed that a greater effect was observed in the group in which WDR34 was inhibited than in the colonies of cells surviving after irradiation with radiation without the treatment with WDR34 siRNA.

<6-2> Checking of Effect of Improving Sensitivity of Brain Cancer Cells to Radiation Through Treatment with siRNA The inhibitory effect on the resistance of cancer cells to radiation through a treatment with a WDR34 inhibitor was checked in the same manner as in Example <6-1>, except that the brain cancer cells (U373) were used instead of the lung cancer stem cells.

As a result, as shown in FIG. 11, it was confirmed that when the treatment with siRNA was performed, colony formation was significantly reduced. Moreover, it was confirmed that in the group irradiated with radiation in a dose of 6 Gy, colony formation by the irradiation with radiation was reduced, but it was confirmed that a greater effect was observed in the group in which WDR34 was inhibited than in the colonies of cells surviving after irradiation with radiation without the treatment with WDR34 siRNA.

From the above results, it can be seen that the WDR34 according to the present invention can regulate the resistance ability of cancer cells, including cancer stem cells, to radiation, and the WDR34 can be a target for a radiation sensitizer used in a radiation treatment.

EXAMPLE 7

Survival Analysis According to WDR34 Gene Expression (Kaplan-Meier)

It was attempted to check that WDR34 is an important factor in the formation of cancer stem cells through in vitro experiments. Therefore, the effect of WDR34 on cancer patients was checked using a data analysis program (Scientific Reports, 2018; 8:9227).

As a result, as shown in FIG. 12, it was confirmed that the survival rate was drastically decreased in the lung cancer patient group and brain cancer patient group with high expression of WDR34.

From the result, it can be seen that when WDR34 is expressed, a cancer treatment may become difficult, and WDR34 can be an important therapeutic target in brain cancer as well as lung cancer.

Hereinbefore, the present invention has been described in detail only with respect to the described embodiments, but it would be obvious to a person with ordinary skill in the art that various variations and modifications are possible within the scope of the technical idea of the present invention, and it goes without saying that such variations and modifications fall within the appended claims.

The invention claimed is:

1. A method for inhibiting cancer stem cells of a cancer patient, comprising administering a composition comprising a WD repeat domain 34 (WDR34) inhibitor as an active ingredient, to a subject in need thereof, wherein the WDR34 inhibitor is an antisense oligonucle-otide, short hairpin RNA (shRNA), or small interfering RNA (siRNA), and wherein the cancer is WDR34-overexpressing cancer selected from the group consisting of liver cancer, brain cancer, and lung cancer.

2. The method of claim 1, wherein the siRNA comprises the sequence of SEQ ID NO: 2 or SEQ ID NO: 3.

3. The method of claim 1, wherein the inhibition of cancer stem cells is at least one of the inhibitions of the formation, self-renewal, invasion, and/or migration of cancer stem cells.

4. The method of claim 1, wherein cancer stem cells of the cancer are cancer stem cells that express one cancer stem cell marker selected from the group consisting of aldehyde dehydrogenase 1 (ALDH1), prominin-1 (CD133; AC122), and hyaluronate receptor (CD44; pglycoprotein 1).

5. The method of claim 1, wherein the cancer is anticancer immune-resistant cancer, resistant cancer, recurrent cancer, or metastatic cancer.

6. The method of claim 1, wherein administering a composition comprising a WD repeat domain 34 (WDR34) inhibitor as an active ingredient inhibits the transformation of cancer cells into cancer stem cells; or inhibits the renewal, invasion, and migration of cancer stem cells.

7. The method of claim 1, wherein the inhibition of cancer stem cells prevents or treats cancer chemoresistance, cancer recurrence, or cancer metastasis during or after a cancer treatment.

8. A method for assisting a radiation anticancer treatment, comprising administering a composition comprising a WD repeat domain 34 (WDR34) inhibitor as an active ingredient, to a subject in need thereof before or together with the radiation, wherein the WDR34 inhibitor is an antisense oligonucle-otide, short hairpin RNA (shRNA), or small interfering RNA (siRNA), and wherein the cancer is WDR34-overexpressing cancer selected from the group consisting of liver cancer, brain cancer, and lung cancer.

9. The method of claim 8, wherein the WDR34 inhibitor enhances the sensitivity of cancer cells, including cancer stem cells, to radiation.

* * * * *